United States Patent
Okada et al.

(10) Patent No.: US 7,429,247 B2
(45) Date of Patent: Sep. 30, 2008

(54) SLEEP STATE ESTIMATING DEVICE AND PROGRAM PRODUCT

(75) Inventors: Shima Okada, Osaka (JP); Yoshihisa Fujiwara, Uji (JP); Yasushi Yamamoto, Hirakara (JP); Fumiiki Yoneda, Moriguchi (JP)

(73) Assignee: Sanyo Electric Co. Ltd., Moriguchi-shi (JP)

( * ) Notice: Subject to any disclaimer, the term of this patent is extended or adjusted under 35 U.S.C. 154(b) by 459 days.

(21) Appl. No.: 11/171,295

(22) Filed: Jul. 1, 2005

(65) Prior Publication Data
US 2006/0009704 A1    Jan. 12, 2006

(30) Foreign Application Priority Data
Jul. 7, 2004    (JP)    .............................. 2004-201155

(51) Int. Cl.
*A61B 5/08*    (2006.01)
(52) U.S. Cl. ........................ 600/534; 600/529
(58) Field of Classification Search ................. 600/529, 600/534
See application file for complete search history.

(56) References Cited

U.S. PATENT DOCUMENTS

| 5,101,831 | A |   | 4/1992 | Koyama et al. |
|---|---|---|---|---|
| 5,280,791 | A |   | 1/1994 | Lavie |
| 5,846,206 | A | * | 12/1998 | Bader .......................... 600/534 |
| 6,752,766 | B2 |   | 6/2004 | Kowallik et al. |
| 2002/0007124 | A1 | * | 1/2002 | Woodward .................. 600/481 |
| 2002/0029004 | A1 | * | 3/2002 | Starr et al. ................... 600/538 |
| 2004/0111041 | A1 | * | 6/2004 | Ni et al. ....................... 600/544 |
| 2005/0209512 | A1 | * | 9/2005 | Heruth et al. ............... 600/301 |
| 2005/0234314 | A1 | * | 10/2005 | Suzuki et al. ................ 600/301 |

FOREIGN PATENT DOCUMENTS

| JP | 2004-049838 A | 2/2004 |
|---|---|---|
| JP | 2004-089267 A | 3/2004 |

OTHER PUBLICATIONS

Office Action of Japan Patent Office dated Feb. 20, 2007 issued in corresponding Japanese Patent Application No. 2004-201155.
D. Hoyer et al.; "Validating Phase Relations Between Cardiac and Breathing Cycles During Sleep", IEEE Engineering in Medicine and Biology, Mar./Apr. 2001.

(Continued)

*Primary Examiner*—Robert L. Nasser, Jr.
*Assistant Examiner*—Christian Y Jang
(74) *Attorney, Agent, or Firm*—Westerman, Hattori, Daniels & Adrian, LLP.

(57) ABSTRACT

A sleep state of a subject is estimated from respiration signals that are readily detected without restraining the subject. From a voltage waveform based on respiratory movement of a person, positive peak values and the (time) interval between adjacent peaks are calculated. Also obtained is the area of a region that is enclosed by the voltage waveform and a time axis between peaks, and the average value and dispersion value of the obtained inter-peak areas are calculated. The calculated values are used to set a preliminary sleep state value for a given period, and sleep state values over plural periods are factored in to estimate a sleep state at a given time point.

16 Claims, 9 Drawing Sheets

OTHER PUBLICATIONS

D. W. Hudgel et al.; "Mechanics of the respiratory system and breathing pattern during sleep in normal humans", The American Physiological Society, 1984, pp. 133-137.

Hisanori Andoh et al.; "Home Health Monitoring System in the Sleep", SICE Annual Conference in Fukui, Aug. 4-6, 2003, Fukui University, Japan, pp. 2416-2419.

Takayuki Ishikawa et al.; "A Study on Sleep Stage Estimation via Non-invasive Air Mattress Sensor", SICE Annual Conference in Fukui, Aug. 4-6, 2003, Fukui University, Japan, pp. 1414-1417.

T. Watanabe et al.; "Estimation of the Sleep Stages from the Bio-Data, Non-invasively Measured in the Sleep", T. SICE, vol. 38, No. 7, Jul. 2002, pp. 39-47.

* cited by examiner

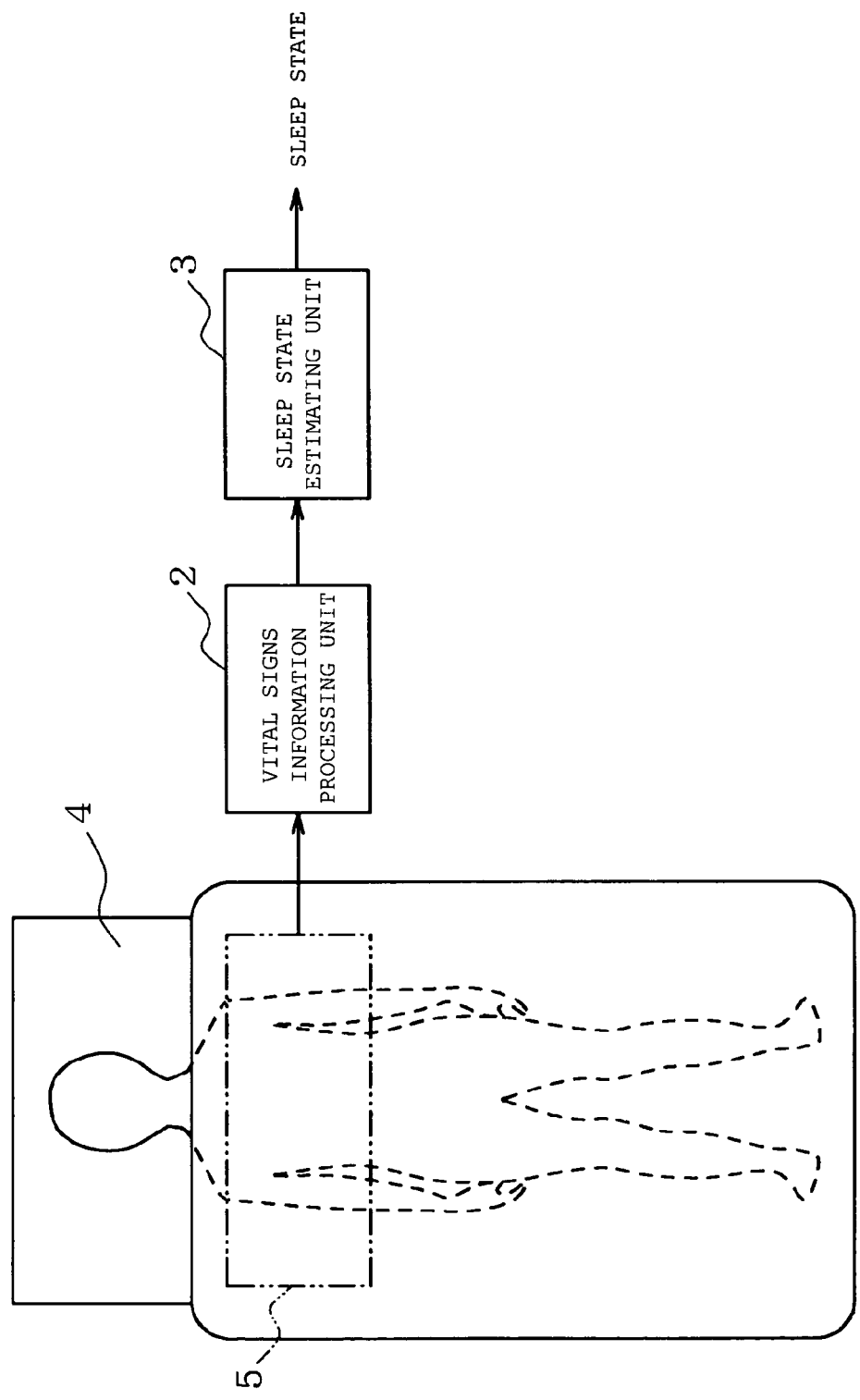

SLEEP STATE ESTIMATING DEVICE AND PROGRAM PRODUCT

This application claims priority under 35 U.S.C. §119 of Japanese Patent Application No. 2004-201155 filed Jul. 7, 2004.

BACKGROUND OF THE INVENTION

1. Field of the Invention

The present invention relates to a sleep state estimating device which estimates a sleep state based on vital signs information, and to a program product for executing a sleep state estimation function.

2. Description of the Related Art

Recently heightened health consciousness among people has created a desire to manage their health by day-to-day sleep control in their household.

During sleep, a person experiences various states through a night. The sleep is divided broadly into two types, namely, REM sleep and non-REM (NREM) sleep. The fact that the NREM sleep alternates with the REM sleep periodically several times during the sleep is known. In general, the sleep undergoes transition as follows. That is, a sleep state during the NREM sleep gradually transits from the light sleep to the deep sleep. After a predetermined duration of the deep sleep state, the sleep state moves toward the light sleep, resulting in the transition to the REM sleep. A finer sleep classification is Sleep Stage. Sleep Stage is regulated by an international standard, and consists of "REM sleep", "Sleep Stages 1, 2, 3, and 4" and, "wakefulness", the "Sleep Stages 1, 2, 3, and 4" being corresponding to the NREM sleep.

Up to now, various methods have been attempted to detect a change in sleep stage. Known examples thereof include polysomnography (PSG) in which electroencephalogram (EEG), electro-oculogram (EOG), electromyogram (EMG), and the like are detected to judge the sleep stage from the waveforms detected. However, the polysomnography requires a large-scale apparatus and can be used only at a site provided with measurement facilities such as a hospital, thereby being unsuitable for daily use such as use in fitness equipment. In addition, the polysomnography can be used for judgment only by a qualified person, and it is not sufficient only that a suitable apparatus is available.

Therefore, it is demanded to detect the change in sleep state with precision by means replacing the polysomnography. Known examples of a method for estimating a sleep stage without using the polysomnography include a method of estimating the sleep stage by applying a neural network theory, a chaos theory, or by using actual measurement data on sleep to measurements of respiration rate, heart rate, and body movement. Those methods for estimation are described in JP 09-294731 A and JP 2001-61820 A, and on pages 581-589 in Vol. 138, No. 7 of collected papers (or Proceedings) published by The Society of Instrument and Control Engineers in 2002.

However, the above-described sleep estimation according to prior art has a problem with a low probability of matching the actual change in sleep state, and much lower accuracy than the polysomnography in judging the deep sleep and the light sleep.

Further, in general, electrocardiogram is used to measure heart rate with precision. Measurement by the electrocardiogram, however, has a drawback in that plural electrodes have to be attached directly to the skin of a subject, restraining the body of a person with the cords extending from each electrode to the measurement equipment. On the other hand, a non-restraining sensor can only catch minute heart rate signals full of noises due to other elements than heartbeat. Non-restraining measurement therefore needs FFT and filter computation processing for frequency analysis as well as signal amplification processing, which complicate the measurement process.

SUMMARY OF THE INVENTION

The present invention has been made in view of the above, and an object of the present invention is therefore to provide a sleep state estimating device capable of estimating how deep or light a subject's sleep is easily with precision while using signals that are readily detected without restraining the subject.

The main feature of the present invention resides in that a sleep state is estimated based on a time-series oriented respiratory movement waveform which changes by the minute regularly and irregularly. A respiratory movement waveform can readily be detected without restraining a subject. The use of a respiratory movement waveform allows simple and accurate estimation of a sleep state.

An aspect of the present invention is characterized by a sleep state estimating device including: waveform obtaining means for obtaining a time-series oriented waveform curve concerning respiration from data provided by a sensor for obtaining vital signs information; and sleep state estimating means for estimating a sleep state based on the waveform shape of the waveform curve obtained by the waveform obtaining means.

A sleep state estimating device according to this aspect uses a time-series oriented waveform curve concerning respiration, and thus makes smooth sleep state estimation possible without restraining a subject too heavily. In addition, since a sleep state is estimated based on the shape of this waveform, an accurate sleep state can be learned and the precision of the sleep state estimation is high.

A sleep state estimating device according to this aspect may be structured such that a sleep state is estimated by comparing an evaluation value, which corresponds to the waveform shape of the time-series oriented waveform curve concerning respiration, against a reference value, which indicates a sleep state. Employed as an evaluation value is, for example, the area of a region enclosed by the waveform curve and a reference axis. The reference axis is a straight line parallel to the time axis that gives a fixed amplitude value. For instance, a linear line that sets the amplitude value to 0 is used as the reference axis.

Measuring the shape of the time-series oriented waveform concerning respiration by its area in this manner makes it simpler to calculate an evaluation value determined in accordance with the waveform shape and makes it possible to track changes in waveform with precision. As a result, a sleep state can be estimated easily and accurately.

The evaluation value described above may be the quotient of a dispersion value of a series of inter-peak areas divided by the square of the average of the inter-peak areas. The term inter-peak area refers to the area of a portion of the region enclosed by the waveform curve and the reference axis that is defined by two adjacent time points where the waveform amplitude value peaks.

Using a dispersion value of inter-peak areas in this manner makes precise sleep state estimation possible. One dispersion value of inter-peak areas does not uniquely determine one sleep state since the body position and the like have to be factored in. Dividing a dispersion value of inter-peak areas by the square of the average of the inter-peak areas which could be greatly influenced by the body position and the like as described above effectively suppresses the influence that a change in body position and the like has over the evaluation value.

A sleep state estimating device according to another aspect of the present invention estimates a sleep state by adding body movement information to the result of comparison between the evaluation value and the reference value. This makes the sleep state estimation even more precise.

A sleep state estimating device according to still another aspect of the present invention estimates a sleep state at a given time point by collecting a sleep state value at regular intervals (a sleep state estimation result of a given period) and using the collected sleep state values of plural periods. According to this aspect, since a sleep state is estimated from plural periods of estimation results, stable sleep estimation is achieved which is less easily affected by a sudden rise or fall of sleep state value.

BRIEF DESCRIPTION OF THE DRAWINGS

The aforementioned and other objects and novel features of the present invention will become more apparent from the following description of an embodiment when taken in conjunction with the accompanying drawings in which:

FIG. 7 shows a sleep state estimating device structure for when a sheet-like, electrostatic capacity type, non-restraining vital signs information sensor is employed;

DETAILED DESCRIPTION OF THE PREFERRED EMBODIMENTS

An embodiment of the present invention is described below with reference to the drawings.

Figure 1:
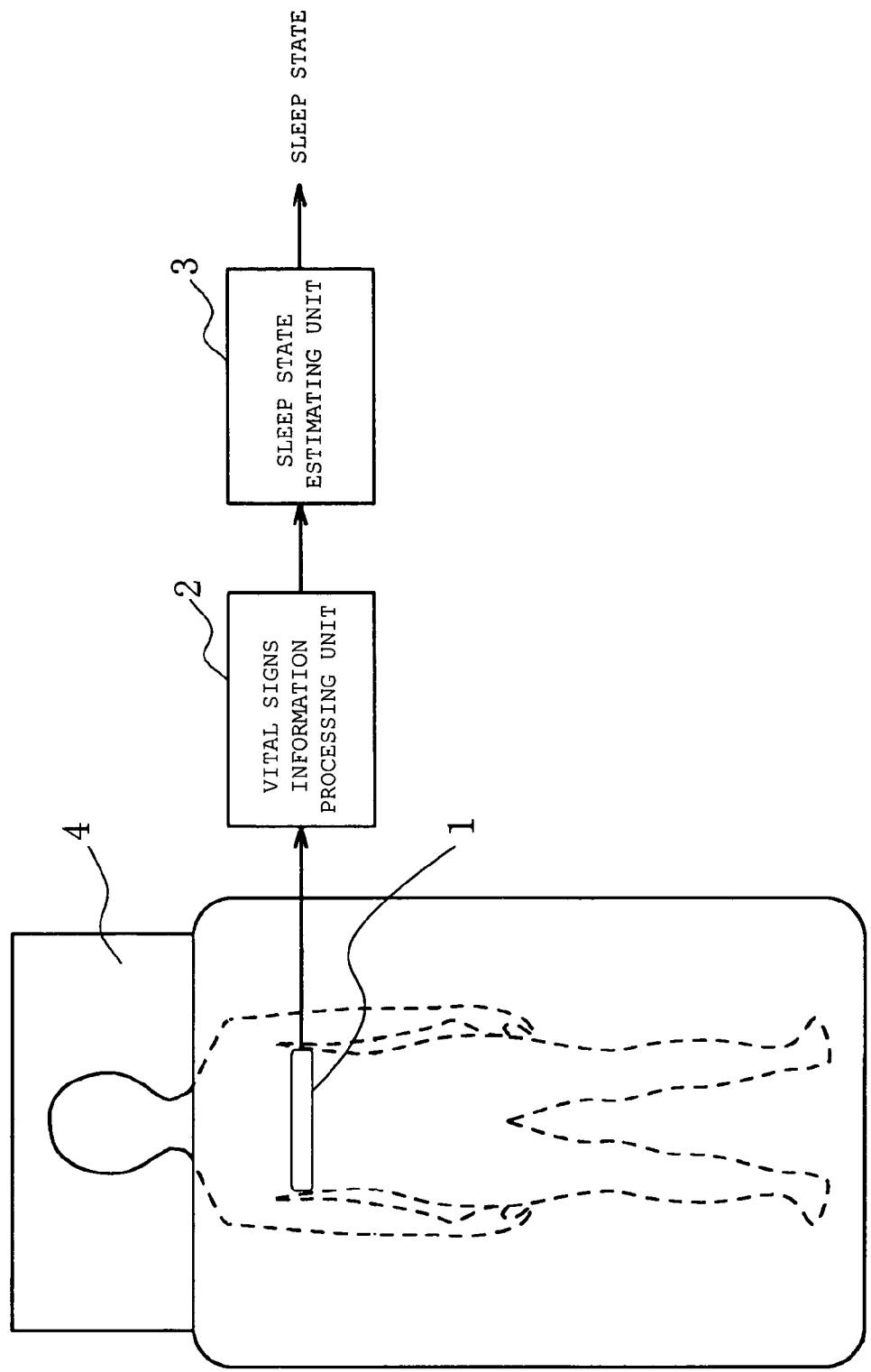
FIG. 1 shows a structure of a sleep state estimating device according to an embodiment of the present invention.

Referring to FIG. 1, a sleep state estimating device according to the embodiment of the present invention is composed of a respiratory band 1, which is one of vital signs information sensors, a vital signs information processing unit 2 including waveform obtaining means for obtaining a waveform curve that is a time-series oriented characteristic concerning respiration from data provided by the sensor, and a sleep state estimating unit 3 for estimating a sleep state. In FIG. 1, a person is lying on a mattress 4 with the respiratory band 1 attached to his/her upper body.

Figure 2:
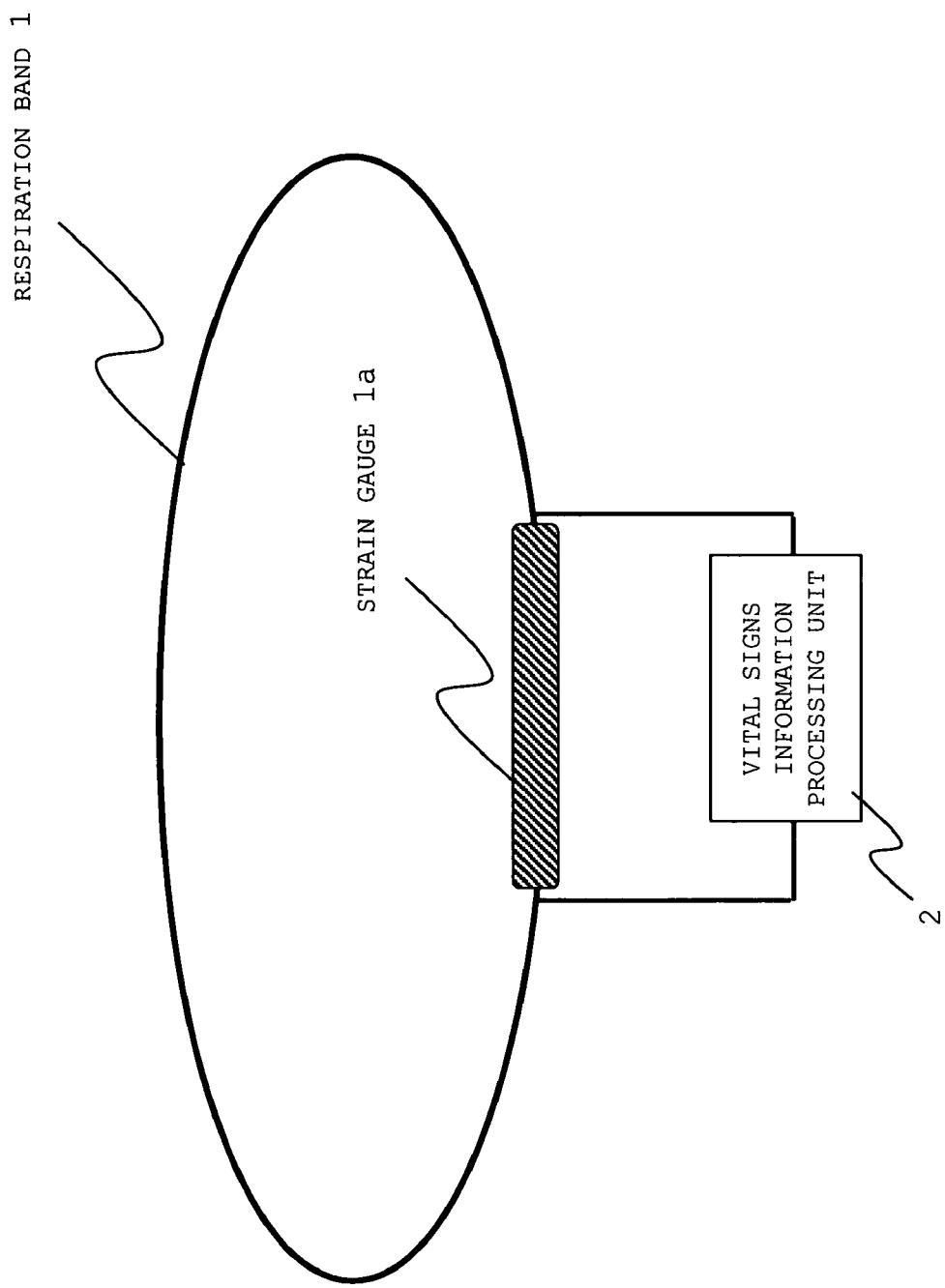
FIG. 2 shows a respiratory band according to the embodiment.

The respiratory band 1 is, as shown in FIG. 2, an elastic band having a strain gauge 1a (for example, an elastic rubber tube having conductive liquid included therein). The respiratory band 1 is wound around the chest or abdominal area of the subject, and respiratory movement of the subject expands and contracts the strain gauge 1a, thereby changing the electric resistance of the gauge.

The vital signs information processing unit 2 converts a resistance shift of the strain gauge 1a into a change in voltage through a bridge circuit or the like and measures the change in voltage of the strain gauge 1a as a change caused by respiratory movement of the subject.

Figure 3:
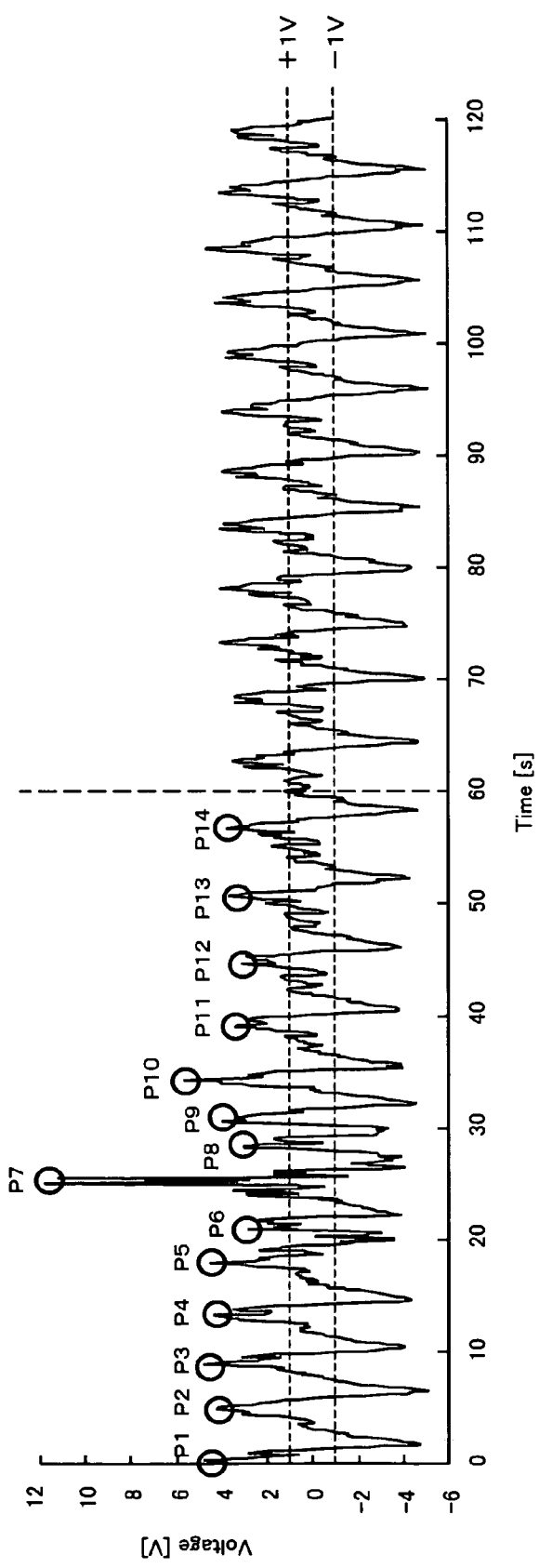
FIG. 3 shows an example of respiratory signal waveform according to the embodiment.

FIG. 3 shows voltage changes which are due to subject's respiratory movement and measured by the vital signs information processing unit 2. In FIG. 3, an axis of abscissa represents measurement time (sec) whereas an axis of ordinate represents voltage (V) when a voltage value is positive, breathing is performed.

In FIG. 3, a large change in waveform in a section between 20 seconds and 30 seconds along the time axis results from a body movement. It is known that a voltage change caused by a body movement is conspicuously larger than the one caused by a respiration movement. Such information from body movement can be utilized in estimating whether a subject is awake (a wake state) or asleep (a state other than the wake state).

The term body movement here includes not only rollovers during sleep but also a body movement during a wake state and a state that can be deemed as a wake state. For instance, an obviously abnormal value or cycle found in vital signs information is treated as an indicator of a wake state.

The sleep state estimating unit 3 samples, at a sampling frequency of 100 Hz, a voltage waveform measured by the vital signs information processing unit 2, to thereby digitize the waveform. Since a body movement can be detected from a change in voltage as described above, this embodiment uses the ratio of n peak values ($V_j[j=1, 2, 3, \ldots, n]$) to detect a body movement (hereinafter referred to a speak value ratio). A peak value is a maximum positive voltage value at which the voltage waveform shape peaks.

In FIG. 3, there are 14 positive peak value points (P1 to P14) within the time section between 0 second and 59 seconds. When the time interval between time points of the peaks (the time of the peak values: $T_j[j=1, 2, 3, \ldots, n]$) (hereinafter referred to as peak interval) is outside of a given range, it can be judged from experiment and research data that a subject is awake or a body movement has occurred. Accordingly, peak intervals are also used to estimate whether a subject is awake.

Peak values and peak intervals are calculated as follows. The maximum value within a window of time from when measured voltage change data exceeds a given positive threshold (1 V in this embodiment) until when the data reaches a given negative threshold (−1 V in this embodiment) is calculated as a positive voltage peak value. Thus setting a negative threshold prevents erroneous detection of a positive peak value due to the hysteresis effect. A time period from a positive peak value calculated to the next positive peak value calculated is set as a peak interval. The peak value ratio and the peak interval are expressed by the following expressions:

Peak value ratio: $PVR_j = V_{j+1}/V_j$

Peak interval: $PI_j = T_{j+1} - T_j [j=1, 2, 3, \ldots, (n-1)]$

A description is given below with reference to flow charts shown FIGS. 4 and 5 on how the sleep state estimating unit 3 estimates the sleep state.

Figure 4:
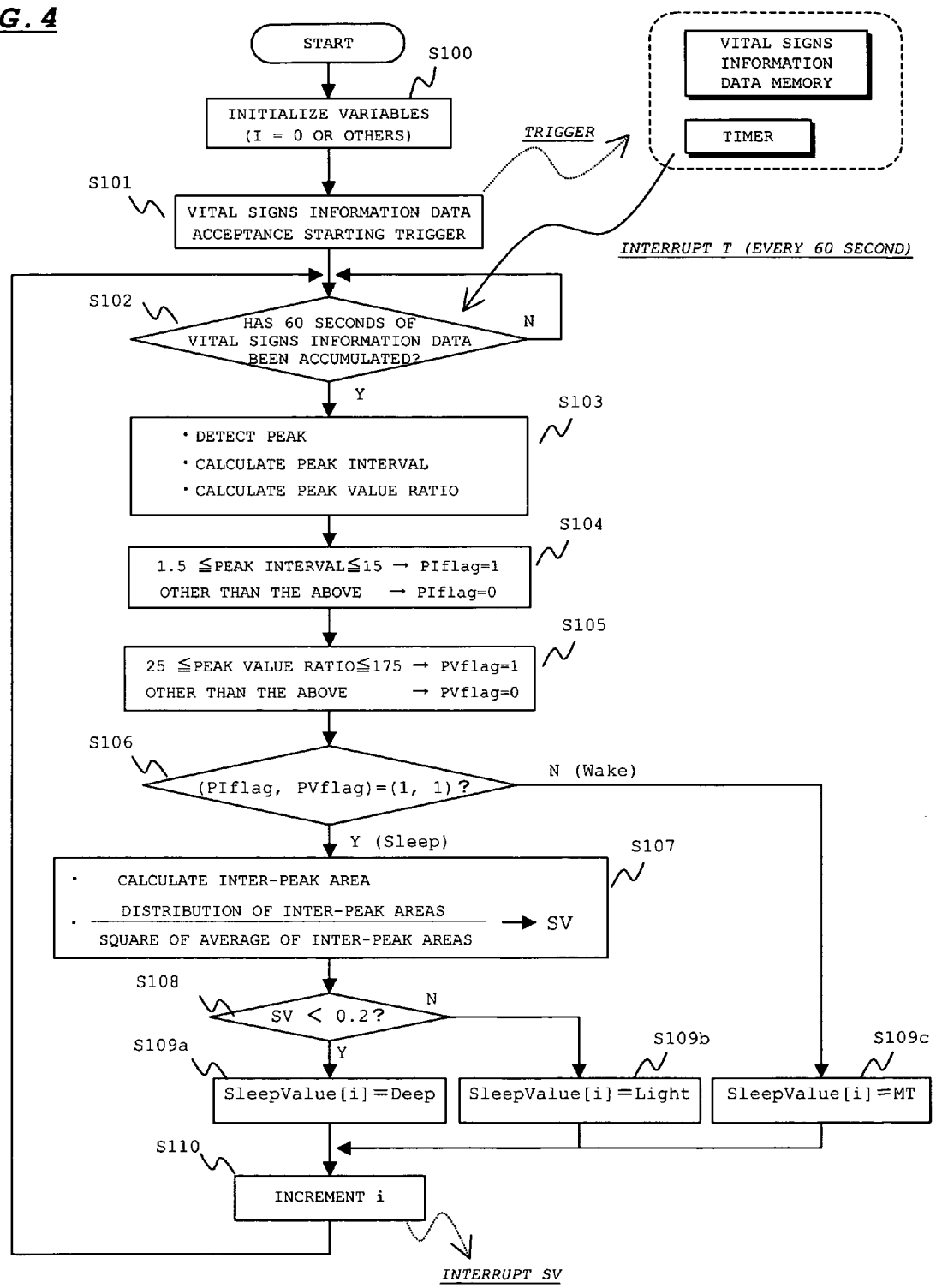
FIG. 4 is a flow chart of processing of estimating a sleep state according to the embodiment.

In Step S100 of FIG. 4, a timer for counting time is reset, and variables (e.g., a loop count variable i), a memory, and the like are cleared.

In Step S101, a trigger signal is applied to have hardware, namely, the timer and the vital signs information data memory, start counting time and taking in vital signs information data. Thus the timer starts counting time and generates an interrupt T signal at regular intervals (every 60 seconds in this embodiment) The vital signs information processing unit 2 starts measuring changes in voltage based on respiration information from the sensor. As the vital signs information processing unit 2 starts measuring, the vital signs information data memory starts taking measurement results (digital data) in.

In Step S102, whether or not the given period, 60 seconds, of data has been accumulated in the vital signs information data memory in time with the interrupt T signal is checked. If 60 seconds of data has been accumulated, the procedure proceeds to Step S103 and, if not, the procedure returns to Step S102.

In Step S103, peak values are detected by the above-described method based on the data accumulated in the vital signs information data memory. From the detection results, peak intervals and the peak value ratio are calculated.

In Step S104, it is judged whether or not every peak interval calculated is within a given range, and a flag PIflag is set to 1 in the case where every peak value is within the range and to 0 in any other cases. The PIflag set to 0 indicates a body movement in a wake state or a state that cannot be deemed as a sleep state.

In Step S105, it is judged whether or not every peak value ratio calculated is within a given range, and a flag PVflag is set to 1 in the case where every peak value ratio is within the range and to 0 in any other cases. The PVflag set to 0 indicates a body movement in a wake state or a state that cannot be deemed as a sleep state.

In Step S106, it is judged whether or not the flags PIflag and PVflag are both set to a given value, 1 ((PIflag, PVflag)=(1, 1)). In the case where (PIflag, PVflag)=(1, 1), the procedure proceeds to Step S107 and, in any other cases, the procedure is branched into Step S109c.

In Step S107, (n−1) inter-peak areas $g_j$ ([j=1, 2, 3, (n−1)]) are calculated from n peak points within a period in question (a 60-second section). Then the average and dispersion of the inter-peak areas are obtained, and an evaluation value SV is calculated by dividing the obtained dispersion value by the square of the obtained average value. The evaluation value SV is a value determined in accordance with the waveform shape of a waveform curve that is a time-series oriented characteristic concerning respiration. In other words, the evaluation value SV represents a respiration state, specifically, steady respiration when the value is small and erratic respiration when the value is large.

The term inter-peak area refers to the area of a region enclosed by the waveform curve and the reference axis between two adjacent peak points. In a section where the voltage value is negative, the absolute value of an integration value is added to the inter-peak area. The reference axis is, as shown in FIG. 3, a straight line parallel to the time axis that keeps the voltage value constant. The reference line in this embodiment is a straight line drawn where the voltage value is zero.

When the average of inter-peak areas is given as A, a dispersion B is expressed by the following expression:

$$B = \frac{\sum_{j=1}^{n-1}(A - g_j)^2}{n-1}$$

Accordingly, the evaluation value SV is expressed by the following expression:

$$SV = B/A^2$$

In Step S108, the evaluation value SV reflecting a respiration state is compared against a reference value which determines a sleep state. If the evaluation value SV is smaller than the reference value, the procedure proceeds to Step S109a and, if not, the procedure is branched into Step S109b. The reference value used in this embodiment is 0.2.

In Steps S109a, S109b, and S109c, sleep state values DEEP, LIGHT, and MT are set, respectively, to SleepValue[i].

In Step S110, the loop count variable i is incremented and an interrupt SV signal, which indicates the end of the sleep state value setting work in this period (a 60-second section), is emitted. Thereafter, the procedure returns to Step S102 in order to start the sleep state estimating routine for the next period (a 60-second section) Subsequently, the sleep state value SleepValue[i] is set for each 60-second section in the same manner.

Figure 5:
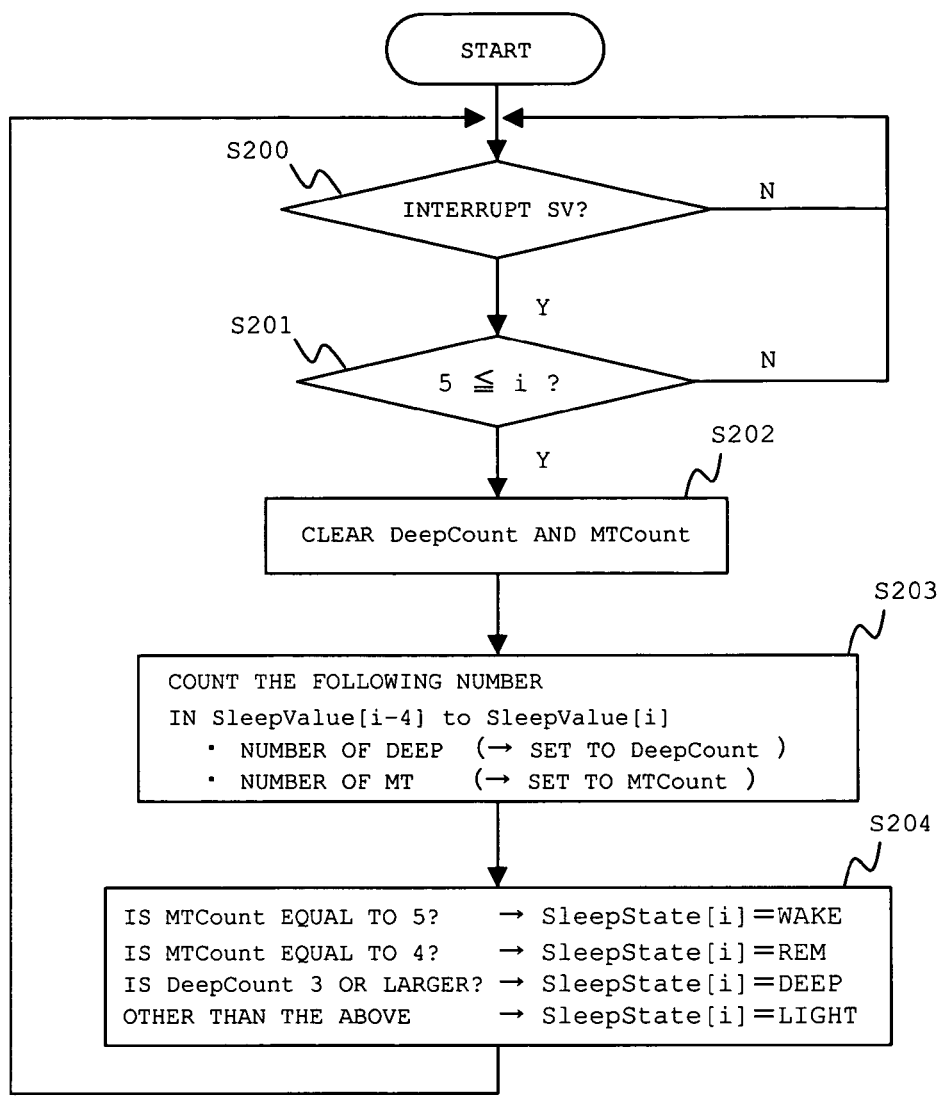
FIG. 5 is a flow chart of processing of estimating a sleep state according to the embodiment.

FIG. 5 is a flow chart of processing of estimating a sleep state with the use of the sleep state value SleepValue[i].

In Step S200 of FIG. 5, whether the interrupt SV signal has been emitted or not is judged. In the case where the interrupt SV signal has been emitted, the procedure proceeds to Step S201.

In Step S201, whether or not the loop count variable i is 5 or larger is judged. In other words, it is judged that whether 5 periods (60-second section×5) of the sleep state value SleepValue[i] has been obtained or not. In the processing flow of FIG. 5, a sleep state at a given time point is estimated with the use of a preset number (five) of periods of sleep state value SleepValue[i]. Therefore, the sleep state estimating unit 3 cannot make a sleep state estimation immediately after the start until the set periods of sleep state values are obtained. This is the reason whether 5 periods of sleep state value SleepValue[i] has been obtained or not is judged in Step S201. If the loop count variable i is 5 or larger, the procedure proceeds to Step S202 and, if not, the procedure returns to Step S200.

In Step S202, count variables DeepCount and MT Count are cleared.

In Step S203, DEEP and MT are counted for each of 5 sleep state values, SleepValue[i−4] to SleepValue[i]. The count of DEEP is set to the variable DeepCount and the count of MT is set to the variable MT Count.

In Step S204, a sleep state is estimated in accordance with the values of the variable DeepCount and the variable MT count. When the variable MT Count is 5, it is estimated as a wake state (WAKE). When the variable MT Count is 4, it is estimated as a REM sleep state (REM). When the variable DeepCount is 3 or larger, it is estimated as a deep sleep state (DEEP). In other cases than the above three, it is estimated as a light sleep (LIGHT). The estimation result, namely, one of "WAKE", "REM", "DEEP", and "LIGHT", is set to the sleep state value SleepState[i].

The set value is the final estimation result of a sleep state at the time point indicated by the loop count variable i.

As has been described, the flags PI flat and PVflag are judged in Step S106 of FIG. 4, and the evaluation value SV is compared against the thresholds in Step S108 to set the sleep state value SleepValue[i] within a period in question (a 60-second section) in Steps S109a to S109c. The sleep state value SleepValue[i] set in Steps S109a to S109c is a preliminary value for sleep state estimation. At this stage, a body movement of rolling over, for example, could erroneously be construed as a wake state in Step S106, and the precision of estimation should be improved more. Accordingly, this embodiment does not employ the sleep estimation value at this stage as the final estimation.

In this embodiment, in Steps S203 and S204 of FIG. 5, a sleep state of a period in question (a 60-second section) is estimated while factoring in the preliminary sleep state values SleepValue[i-4] to SleepValue[i-1], which are history information of the periods prior to the period in question. The precision of sleep state estimation is thus improved.

Alternatively, a sleep state may be estimated by factoring in sleep state values of periods following a period in question in addition to past sleep state values.

Though not described in detail in this embodiment, the sleep state value of each period may be weighted in estimating a sleep state. For instance, in the case where the variable DeepCount is calculated from SleepValue[3] to SleepValue[7] in order to determine SleepState[5], the sleep state values are weighted in a varied manner by counting the deep count as 0.5 instead of 1 when SleepValue[3] or SleepValue[7] is DEEP and as 2 instead of 1 when SleepValue[5] is DEEP. In this way, an even more improvement can be expected in precision of sleep state estimation.

The estimated sleep state "WAKE" in Step S204 corresponds to "Stage W (wakefulness)" according to the aforementioned definition of sleep stages regulated by the international standard, "REM" corresponds to "Stage REM (REM sleep)", "LIGHT" corresponds to "Sleep Stages 1 and 2", and "DEEP" corresponds to "Sleep Stages 3 and 4".

As described above, the sleep state estimating unit 3 judges whether a subject is in a wake state or not from peak intervals and the peak value ratio, and then judges whether the subject is in a deep sleep state or a light sleep state from the average and dispersion of inter-peak areas of a respiratory movement waveform. The sleep state estimating unit 3 further factors in estimation results over plural sections to improve the precision of sleep state estimation even more greatly.

Figure 6A:
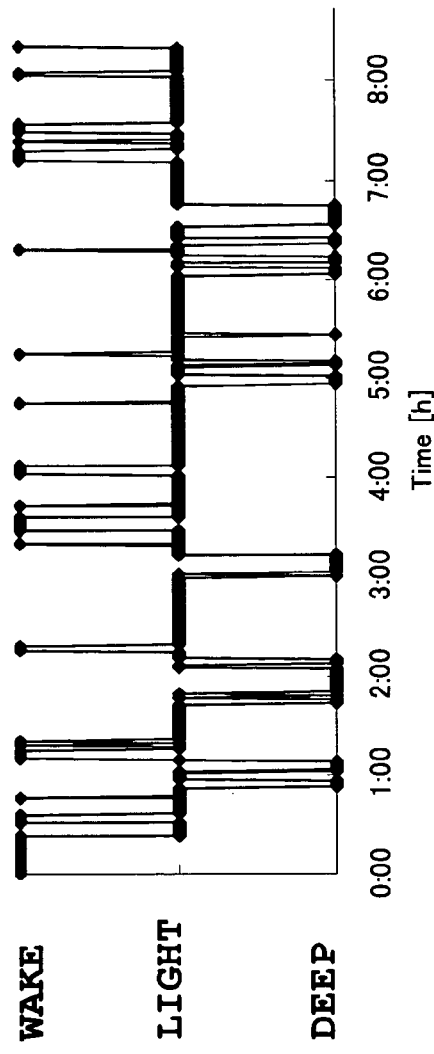
FIGS. 6A and 6B are graphs in which sleep state estimation results provided by the sleep state estimating device according to the embodiment are compared with actual sleep stage data measured by polysomography.
Figure 6B:
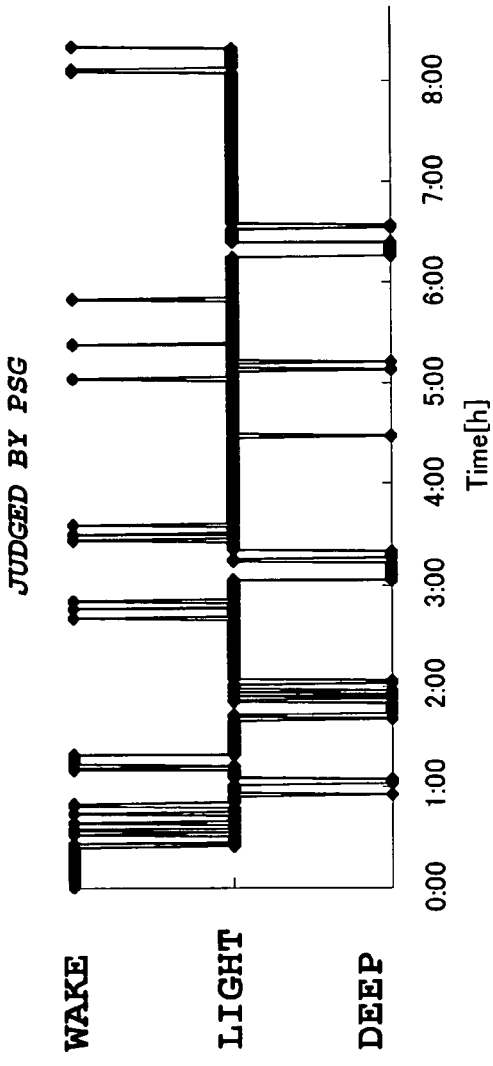

FIGS. 6A and 6B show, for comparison, sleep state estimation results according to this embodiment and sleep state estimation results according to PSG, respectively. In FIGS. 6A and 6B, estimations "REM" and "LIGHT" are phrased as "light" and an estimation "DEEP" is phrased as "deep".

A comparison between FIGS. 6A and 6B shows that estimation results according to this embodiment and results according to PSG roughly coincide in the time it takes for a subject to enter into a light sleep since lying down, the time point the subject enters a deep sleep after 1 to 3 hours, the sleep cycle, and the like. This confirms that sleep state estimation according to this embodiment is made with high precision.

Sleep state estimation from respiratory movement identifies the sleep state after seven hours as a wake state whereas it is identified as a light sleep by PSG. A possible cause of the difference is that a frequent body movement at dawn is construed as a wake state in this embodiment. It is a known sleep characteristic that body movement increases as daybreak approaches. The estimation results according to PSG are judging results based on the method of Allan Rechtschaffen & Anthony Kales. Judging results by PSG sometimes do not match the actual state of a subject since a judgment can be warped by a judge's subjectivity.

Figure 8:
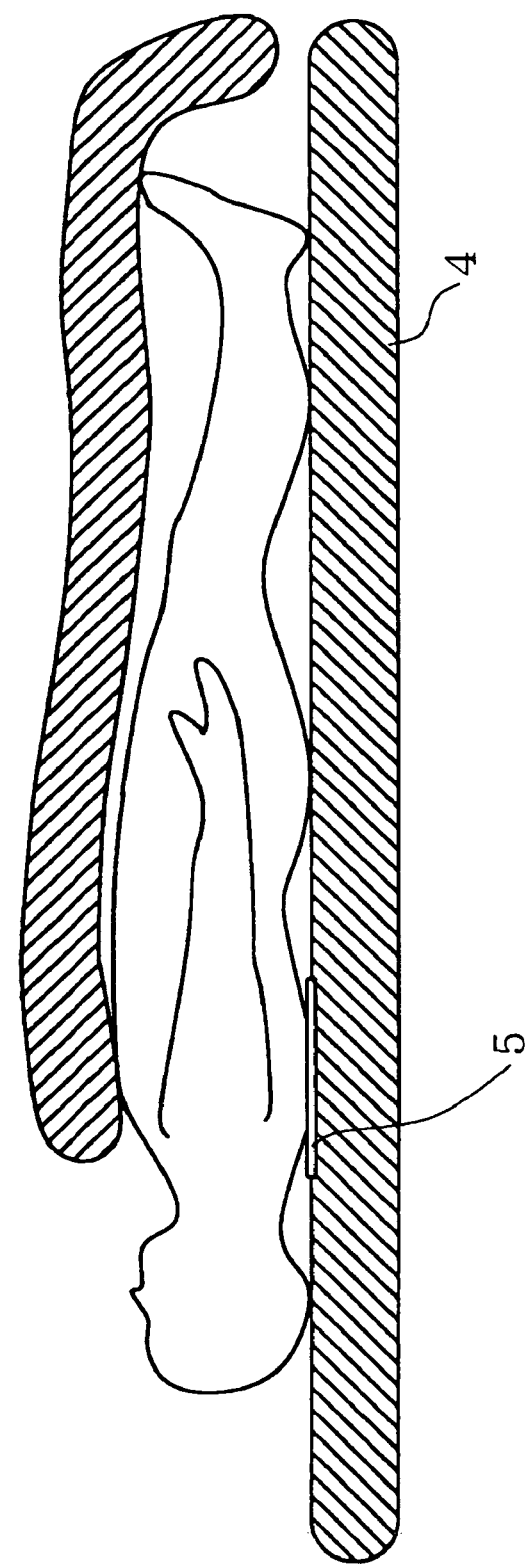
FIG. 8 shows a sleep state estimating device structure for when the sheet-like, electrostatic capacity type, non-restraining vital signs information sensor is employed.

The above-described embodiment uses a respiration band as a vital signs information sensor. An alternative vital signs information sensor is a non-restraining sensor, for example, a sheet-like electrostatic capacity type sensor. In this case, a sheet-like electrostatic capacity type sensor 5 is attached to the mattress 4 as shown in FIGS. 7 and 8.

The sheet-like electrostatic capacity type sensor 5 is pressed down by the upper body of a person, thus changing the distance between electrodes and, accordingly, the electrostatic capacity of the sheet-like electrostatic capacity type sensor 5 is changing. Therefore, the vital signs information processing unit 2 in this case measures data of changes in electrostatic capacity of the sheet-like electrostatic capacity type sensor 5 caused by human respiratory movement and body movement. To give a specific example, the resonant frequency of the electrostatic capacity is measured with an LC resonant circuit. The sleep state estimating unit 3 in this case estimates a sleep state using an electrostatic capacity changing waveform curve based on human respiratory movement and body movement which is an output signal of the vital signs information processing unit 2. Specifics of how the sleep state estimating unit 3 estimates a sleep state from this waveform curve are identical with those in the above-described example in which a respiration band is employed.

Figure 9A:
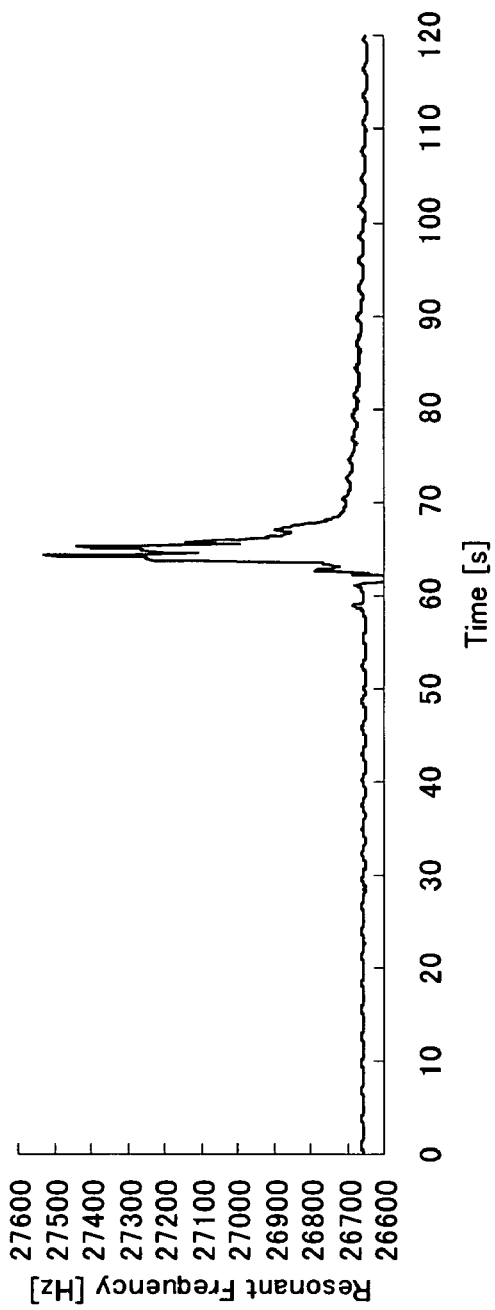
FIGS. 9A and 9B show an example of respiratory signal waveform extracted when employing the sheet-like, electrostatic capacity type, non-restraining vital signs information sensor.
Figure 9B:
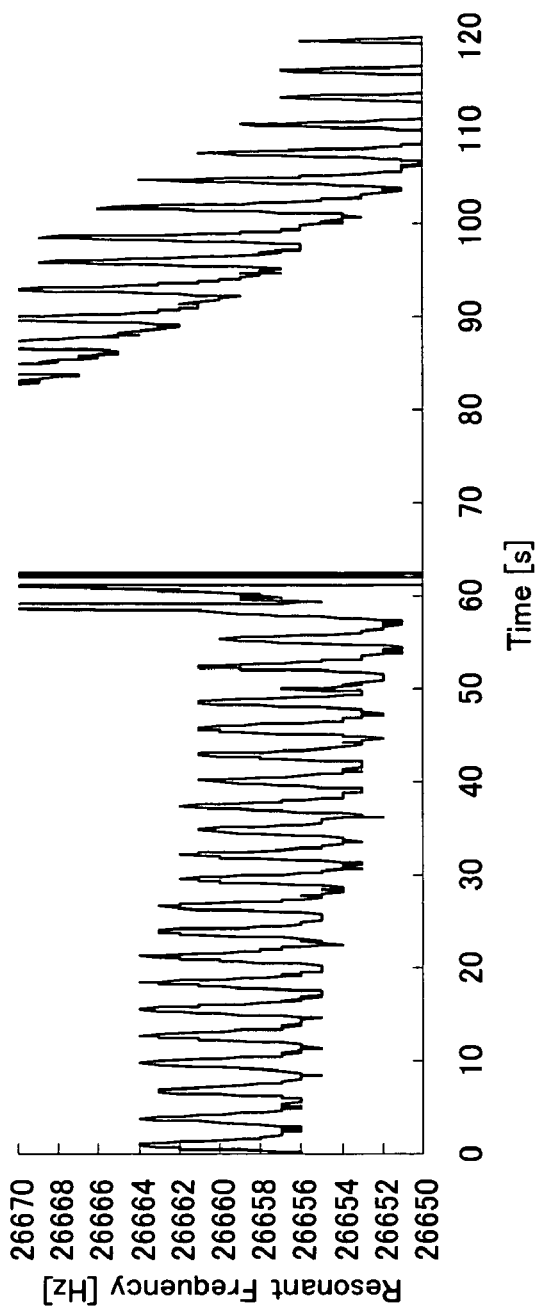

FIGS. 9A and 9B show voltage changes caused by human respiratory movement and body movement and measured by the vital signs information processing unit 2. The sampling frequency here is 10 Hz. In FIGS. 9A and 9B, the axis of abscissa represents a measurement time (sec) and the axis of ordinate represents a resonant frequency (Hz). FIG. 9B is a diagram obtained by enlarging FIG. 9A in the direction of the axis of ordinate by narrowing the range of the axis of ordinate, so that the waveform of respiratory movement can easily be checked out.

In FIGS. 9A and 9B, there are changes in waveform caused by a body movement around 60 seconds to 100 seconds along the time axis. Thus, a frequency change caused by a body movement is far larger than the one caused by a respiration movement. This waveform is about the resonant frequency, and can be used in calculation, estimation, and the like as in the above-described embodiment by setting appropriate thresholds.

In the above-described embodiment, the sleep state estimating unit 3 samples, at a sampling frequency of 100 Hz, voltage changes measured by the vital signs information processing unit 2, to thereby digitize the voltage changes, calculate speak interval values and peak values based on voltage measurement results of 60 seconds, which is a given section, and estimates a sleep state using calculated peak interval values, peak values and an evaluation value which is calculated from the average and dispersion of inter-peak areas. The sampling frequency, the thresholds, and the length of one section can be changed suitably. For thresholds to the peak interval value and the like used by the sleep state estimating unit 3 in estimating a sleep state, values tuned by performing statistical processing on data collected from plural subjects are applied.

Hardware suitable to execute the processing flows shown in FIGS. 4 and 5 is a CPU, memory, and other LSIs of any computer. The processing flows of FIGS. 4 and 5 may be executed by software, such as a program loaded onto a memory. The function blocks shown in FIG. 1 to illustrate the configuration of the sleep state estimating device can take various forms including hardware, software, and a combination of hardware and software. For instance, the sleep state estimating device can be a personal computer in which programs for executing the functions of the vital signs information processing unit 2 and the sleep state estimating unit 3 or the processing of FIGS. 4 and 5 are installed. The programs may be installed in the personal computer by loading an optical disk or magnetic disk holding the programs into the personal computer. Alternatively, the programs may be installed in the personal computer by data transmission via the Internet.

The above description on the embodiment of the present invention is not to limit the present invention. The embodiment of the present invention can suitably be modified in various ways within the scope of the technical idea described in claims of the present invention.

What is claimed is:

1. A sleep state estimating device, comprising:
   waveform obtaining means for obtaining a time-series oriented waveform curve concerning respiration from data provided by a sensor for obtaining vital signs information; and
   sleep state estimating means for estimating a sleep state based on a waveform shape of the waveform curve obtained by the waveform obtaining means,
   wherein the sleep state is estimated by comparing an evaluation value with a reference value, the evaluation value being an area of a region enclosed by the waveform curve and a reference axis.

2. A sleep state estimating device according to claim 1, wherein the sleep state estimating means comprises:
   evaluation value calculating means for calculating the evaluation value; and
   comparing means for comparing the evaluation value calculated by the evaluation value calculating means against the reference value, wherein the reference value indicates a sleep state.

3. A sleep state estimating device according to claim 2, wherein the evaluation value calculating means comprises area calculating means for calculating the area of the region enclosed by the waveform curve and the reference axis.

4. A sleep state estimating device according to claim 3, wherein the evaluation value calculating means further comprises:
   peak calculating means for calculating, from data provided by the sensor, peak time points that are each obtained when the waveform shape peaks; and
   inter-peak area calculating means for calculating an area of a region enclosed by the waveform curve and the reference axis between peak time points.

5. A sleep state estimating device according to claim 4, wherein an evaluation value calculated by the evaluation value calculating means is the quotient of a dispersion value of inter-peak areas divided by the square of the average of the inter-peak areas.

6. A sleep state estimating device according to claim 5, further comprising body movement information obtaining means for obtaining body movement information,
   wherein the sleep state estimating means sets a sleep state value based on body movement information from the body movement information obtaining means and an estimation result from the comparing means.

7. A sleep state estimating device according to claim 6, wherein the sleep state estimating means sets the sleep state value for each given period, and estimates a sleep state at a given time point from sleep state values accumulated for plural periods which are set in advance.

8. A sleep state estimating device according to claim 7, wherein the sleep state estimating means estimates a sleep state by weighting sleep state values of the respective periods.

9. A computer readable storage medium for use in a computer, the computer readable storage medium being encoded with a computer program causing the computer to execute a sleep state estimating method, comprising:
   a waveform obtaining step of obtaining a time-series oriented waveform curve concerning respiration from data provided by a sensor for obtaining vital signs information; and
   a sleep state estimating step of estimating a sleep state based on a waveform shape of the waveform curve obtained in the waveform obtaining step, the sleep state estimating step comprising comparing an evaluation value with a reference value, the evaluation value being an area of a region enclosed by the waveform curve and a reference axis.

10. A computer readable medium according to claim 9, wherein the sleep state estimating step comprises:
    an evaluation value calculating step of calculating the evaluation value; and
    a comparing step of comparing the evaluation value calculated in the evaluation value calculating step against the reference value, wherein the reference value indicates a sleep state.

11. A computer readable medium according to claim 10, wherein the evaluation value calculating step comprises an area calculating step of calculating the area of the region enclosed by the waveform curve and the reference axis.

12. A computer readable medium according to claim 11, wherein the evaluation value calculating further comprises:
    a peak calculating step of calculating, from data provided by the sensor, peak time points that are each obtained when the waveform shape peaks; and
    an inter-peak area calculating step of calculating an area of a region enclosed by the waveform curve and the reference axis between peak time points.

13. A computer readable medium according to claim 12, wherein an evaluation value calculated in the evaluation value calculating step is the quotient of a dispersion value of inter-peak areas divided by the square of the average of the inter-peak areas.

14. A computer readable medium according to claim 13, further comprising a body movement information obtaining step of obtaining body movement information,
    wherein the sleep state estimating step includes setting a sleep state value based on body movement information from the body movement information obtaining step and an estimation result from the comparing step.

15. A computer readable medium according to claim 14, wherein the sleep state estimating step includes setting the sleep state value for each given period, and estimating a sleep state at a given time point from sleep state values accumulated for plural periods which are set in advance.

16. A computer readable medium according to claim 15, wherein the sleep state estimating includes estimating a sleep state by weighting sleep state values of the respective periods.

* * * * *